United States Patent
Jegham et al.

Patent Number: 5,969,146
Date of Patent: Oct. 19, 1999

[54] OXAZOLIDIN-2-ONE DERIVATIVES, PREPARATION METHOD THEREFOR AND THERAPEUTICAL USE THEREOF

[75] Inventors: Samir Jegham, Argenteuil; Frédéric Puech, Rueil Malmaison; Philippe Burnier, Maisons Laffitte; Danielle Berthon, Mareil Marly; Odile Leclerc, Rueil Malmaison, all of France

[73] Assignee: Synthelabo, Le Plessis Robinson, France

[21] Appl. No.: 09/051,539

[22] PCT Filed: Oct. 8, 1996

[86] PCT No.: PCT/FR96/01511

§ 371 Date: Apr. 13, 1998

§ 102(e) Date: Apr. 13, 1998

[87] PCT Pub. No.: WO97/13768

PCT Pub. Date: Apr. 17, 1997

[30] Foreign Application Priority Data

| | | | |
|---|---|---|---|
| Oct. 11, 1995 | [FR] | France | 95 11902 |
| Jul. 25, 1996 | [FR] | France | 96 09361 |
| Jul. 25, 1996 | [FR] | France | 96 09362 |

[51] Int. Cl.⁶ .......... C07D 413/04; C07D 413/14; A61K 31/42

[52] U.S. Cl. .......... 548/232; 548/225; 548/229; 514/374

[58] Field of Search .......... 548/225, 229, 548/232; 514/374

[56] References Cited

U.S. PATENT DOCUMENTS 5,783,590 7/1998 Booher et al. .......... 514/374

FOREIGN PATENT DOCUMENTS

| | | |
|---|---|---|
| 0006524 | 1/1980 | European Pat. Off. . |
| 0657440 | 6/1995 | European Pat. Off. . |
| 4425609 | 1/1996 | Germany . |

*Primary Examiner*—Floyd D. Higel
*Attorney, Agent, or Firm*—Jacobson, Price, Holman & Stern, PLLC

[57] ABSTRACT

Compounds derived from oxazolidin-2-one of formula (I)

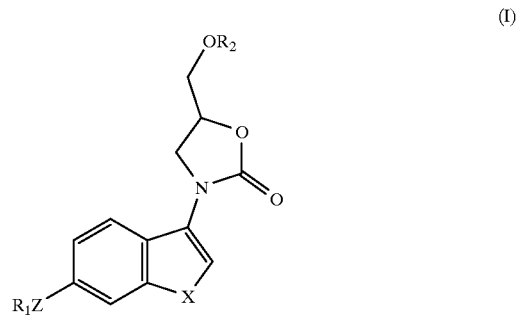

in which:

$R_1$ represents a hydrogen atom, an alkyl group, a hydroxyalkyl group, a fluoroalkyl group, a hydroxyfluoroalkyl group, a cyanoalkyl group, a substituted or unsubstituted phenyl group, a substituted or unsubstituted phenylmethyl group or an $R_3A$- group in which $R_3$ is a cycloalklyl or cyclooxyalkyl group which is unsubstituted or substituted by a hydroxyl group and A is a —$CH_2$ or —$CH_2$—$CH_2$ radical, $R_2$ represents a hydrogen atom or a methyl group, X represents an oxygen or sulphur atom or an $NR_4$ group where $R_4$ is an alkyl group or a hydrogen atom, and Z represents an oxygen atom or a —CH=CH or —$CH_2$—$CH_2$ group, their process of preparation and their applications in therapeutics.

20 Claims, No Drawings

OXAZOLIDIN-2-ONE DERIVATIVES, PREPARATION METHOD THEREFOR AND THERAPEUTICAL USE THEREOF

This application is a 371 of PCT/FR96/01511 filed Oct. 8, 1996.

The subject of the present invention is compounds derived from oxazolidin-2-one of general formula (I)

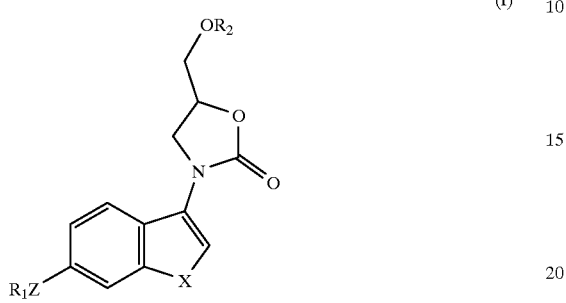

in which:

$R_1$ represents a hydrogen atom, an alkyl group, a hydroxyalkyl group, a fluoroalkyl group, a hydroxyfluoroalkyl group, a cyanoalkyl group, a phenyl group which is unsubstituted or substituted by a halogen atom or by an alkoxy, nitrile or nitro group, a phenylmethyl group which is unsubstituted or substituted by a halogen atom or by an alkoxy, nitrile or nitro group or an $R_3A$- group in which $R_3$ is a is cycloalkyl or cyclooxyalkyl group which is unsubstituted or substituted by a hydroxyl group and A is a —$CH_2$ or —$CH_2$—$CH_2$ radical, $R_2$ represents a hydrogen atom or a methyl group, X represents an oxygen or sulphur atom or an $NR_4$ group where $R_4$ is an alkyl group or a hydrogen atom and Z represents an oxygen atom or a —CH=CH or —$CH_2$—$CH_2$ group, their process of preparation and their therapeutic applications.

In the context of the present invention, and except when otherwise indicated, the above terms have the following meanings:

an alkyl group is a linear or branched saturated aliphatic group comprising 1 to 5 carbon atoms, an alkoxy group is an $OR_5$ group, where $R_5$ is an alkyl group as defined above, a fluoroalkyl group is an alkyl group as defined above, at least one of the carbon atoms of which is substituted by one or a number of fluorine atoms, a hydroxyfluoroalkyl group is a fluoroalkyl group as defined above, one of the carbon atoms of which is substituted by a hydroxyl group, a cycloalkyl group is a radical derived from a cycloalkane comprising from 3 to 6 carbon atoms, a cyclooxyalkyl group is a cycloalkyl group as defined above, one of the carbon atoms of which is replaced by an oxygen atom as heteroatom; the perhydrofuranyl and perhydropyranyl groups are representative of such a cyclooxyalkyl group, a cyanoalkyl group is an alkyl group as defined above, at least one of the carbon atoms of which is substituted by a nitrile group.

The compounds of formula (I) where $R_2$ is a methyl group are preferred. Among the latter compounds, those where X represents an oxygen atom are very particularly preferred.

When X represents an oxygen atom, the $R_1Z$ group advantageously represents:

either, i) an $R_aO$ group, where $R_a$ has one of the meanings of $R_1$ chosen from a hydrogen atom, an alkyl group, a fluoroalkyl group, a hydroxyfluoroalkyl group, a cyanoalkyl group, an $R_3A$- group, a phenyl group which is unsubstituted or substituted by a halogen atom or a nitro, nitrile or alkoxy group and a phenylmethyl group which is unsubstituted or substituted by a halogen atom or a nitro, nitrile or alkoxy group. More preferentially, $R_a$ is a hydrogen atom or a phenylmethyl, butyl, 4,4,4-trifluorobutyl, 4,4,4-trifluoro-3-hydroxybutyl, 3,3,3-trifluoro-2-hydroxypropyl, 3-cyanopropyl, p-fluorophenylmethyl, cyclopropylmethyl or 2-(1-hydroxycyclopentyl)ethyl group.

or, ii) an $R_bZ$ group, where Z is a —CH=CH— or —CH—$CH_2$- group and Re has one of the meanings of $R_1$ chosen from a hydrogen atom or an alkyl group, a fluoroalkyl group, a hydroxyalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or a nitro, nitrile or alkoxy group. More preferentially, $R_bZ$ is chosen from the ethenyl, 2-phenylethenyl, 2-phenylethyl, 5,5,5-trifluoropentyl, 5,5,5-trifluoropentenyl, 5,5,5-trifluoro-4-hydroxypentyl or 5,5,5-trifluoro-4-hydroxypentenyl group.

When X represents a sulphur atom, the $R_1Z$ group advantageously represents an $R_cO$ group, where R, has one of the meanings of $R_1$ chosen from an alkyl group, a hydroxyalkyl group, a fluoroalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or by an alkoxy, nitrile or nitro group. According to a preferred aspect of the invention, $R_c$ is chosen from the group consisting of butyl, 4,4,4-trifluorobutyl, 4,4,4-trifluoro-3-hydroxybutyl and the phenylmethyl group.

When X represents an $NR_4$ group, $R_4$ is preferably a methyl group and the $R_1Z$ group advantageously represents an $R_dO$ group, where $R_d$ has one of the meanings of $R_1$ chosen from a fluoroalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or a nitro, nitrile or alkoxy group. According to a preferred aspect of the invention, $R_d$ is chosen from the group consisting of 4,4,4-trifluorobutyl, 4,4,4-trifluoro-3-hydroxybutyl and the phenylmethyl group.

The compounds of formula (I) contain one or two asymmetric carbon atoms. They can therefore exist in the form of pure enantiomers or diastereoisomers or of a mixture of these different forms, including a racemic mixture. These different forms, and their mixtures, form part of the invention.

The compounds of formula (I) in which $R_1Z$ represents an $R_1$—CH=CH— group, with the exception of the compounds in which $R_1$ is a hydrogen atom, exist in the form of cis or trans isomers. These forms, and their mixtures, form part of the invention.

The compounds of the invention of formula (I) can be prepared according to the processes described in Appendices 1 and 2.

The compounds of formulae (Ia), (Ib), (Ic), (Id) and (Ie), which are compounds of formula (I) according to the invention where Z represents an oxygen atom, can be prepared according to the process represented in Appendix 1. In these compounds, X has one of the meanings given in the formula (I). According to this process, an ethyl carbamate derivative of formula (II) is reacted with 4-(methoxymethyl)-1,3-dioxolan-2-one of formula (III) in the presence of potassium carbonate. In the formula (II), $R_1$ and X have one of the meanings given in the formula (I) with the exception, as regards $R_1$, of hydrogen. This reaction makes it possible to obtain a compound of formula (Ia), which is a compound of formula (I) in which $R_2$ represents a methyl group and $R_1$ has one of the meanings given in the formula (I), with the exception of hydrogen.

The compounds of formula (Ia) where $R_1$ represents a phenylmethyl group can be used to prepare the compounds of formula (Ib). The latter are compounds of formula (I) in which $R_1$ represents a hydrogen atom and $R_2$ represents a methyl group. To this end, the phenylmethyl group of the said compound of formula (Ia) is removed by means, for example, of dimethylphenylamine and of aluminium chloride or by catalytic hydrogenation in the presence of palladium-on-charcoal.

The compounds of formula (Ib) can be used to prepare the compounds of formula (Ic). The latter are compounds of formula (I) in which $R_1$ and $R_2$ each represent a hydrogen atom.

To do this, a compound of formula (Ib) is demethylated by means of a Lewis acid, such as boron tribromide, in a solvent such as dichloromethane.

The compounds of formula (Ic) can, in their turn, be used to prepare compounds of formula (Id). The latter are compounds of formula (I) in which $R_1$ has one of the meanings given in the formula (I), with the exception of the hydrogen atom, and $R_2$ is a hydrogen atom. To do this, a compound of formula (Ic) can be reacted with a compound of formula $R_1Y$, where $R_1$ has one of the meanings given in the formula (I), with the exception of hydrogen, and Y is a halogen atom or a labile group, such as methylsulphonyloxy (mesyloxy) or p-toluenesulphonyloxy (tosyloxy). This reaction can be carried out in the presence of a base, such as potassium carbonate, in a solvent, such as acetonitrile, N,N-dimethylformamide or a mixture of these solvents. The reaction temperature can be the reflux temperature of the solvent.

According to an advantageous aspect of the invention, the compounds of formula (Ib) can be used to obtain compounds of formula (Ie) according to the invention in which $R_1$ has one of the meanings given in the formula (I), with the exception of the hydrogen atom meaning. To this end, a compound of formula (Ib) is reacted with a compound of formula $R_1Y$, where $R_1$ has one of the meanings given in the formula (I), with the exception of a hydrogen atom, and Y is as defined above. This reaction can be carried out in the presence of a base, such as potassium carbonate, in a solvent such as acetonitrile. The reaction temperature can be the reflux temperature of the solvent. The compound of formula (Ie) thus obtained can then be demethylated to prepare a compound of formula (Id). The demethylation can be carried out under the conditions indicated above as regards the demethylation of the compound of formula (Ib). Of course, a compound (Ia) which already exhibits the desired meaning of $R_1$ has not to be converted to a compound (Ie); such a compound of formula (Ia) can itself be demethylated to obtain a compound of formula (Id) directly.

According to another aspect of the invention, the compounds of formula (I) in which the $R_1$ group is a group comprising a hydroxyl functional group can be prepared by reacting a compound of formula (II) containing such an $R_1$ group with a compound of formula (III), the said hydroxyl functional group being protected beforehand, in a conventional way for the person skilled in the art, by a protective group, such as t-butyldimethylsilyl. After preparing the compound of formula (Ia), the protective group can be removed from the hydroxyl functional group by means, for example, of tetra-n-butylammonium fluoride, in an organic solvent such as tetrahydrofuran.

The compounds of formulae (If) and (Ig), which are compounds of formula (I) according to the invention where Z represents, respectively, a —CH=CH or —CH$_2$—CH$_2$ group, can be prepared according to the process represented in Appendix 2. In these compounds, X has one of the meanings indicated in the formula (I).

According to this process, a compound of formula (Ib), as mentioned above, is reacted with trifluoromethanesulphonic anhydride (Tf$_2$O) to obtain a trifluoromethanesulphonate derivative of formula (IV).

The compound of formula (IV) can then be reacted with palladium acetate in the presence of carbon monoxide and of methanol to prepare a methoxycarbonyl derivative of formula (V), which is treated, in its turn, by means of a borane-dimethyl sulphide complex (BH$_3$.S(CH$_3$)$_2$) to obtain a hydroxymethyl derivative of formula (VI). The latter can then be treated with oxalyl chloride and dimethyl sulphoxide to prepare a formyl derivative of formula (VII). This treatment can be carried out at a temperature of the order of $-70°$ C.

The formyl derivative of formula (VII) can then be reacted with a triphenylphosphonium salt of formula $R_1CH_2P^+(C_6H_5)_3W^-$, in particular a triphenylphosphonium halide, such as a triphenylphosphonium bromide, where $R_1$ has one of the meanings given in the formula (I) and $W^-$ represents the anion of a halogen atom. This reaction can be carried out in the presence of a base, such as potassium carbonate. A compound according to the invention of formula (If) can thus be prepared in which Z represents a —CH=CH— group.

The compound of formula (If) can then be reduced to prepare a compound according to the invention of formula (Ig). This reduction can be carried out by means of hydrogen in the presence of a catalyst, such as palladium-on-charcoal. In the compounds of formulae (IV), (V), (VI) and (VII), X has one of the meanings given in the formula (I). The compounds of formulae (If) and (Ig) can be demethylated to result in the corresponding compounds of formula (I) where $R_2$ represents a hydrogen atom. This demethylation can be carried out by means of a Lewis acid, such as boron tribromide.

According to an advantageous aspect of the invention, the compounds of formula (If) in which $R_1$ is a hydrogen atom can be prepared directly by reacting the compound of formula (IV) mentioned above with tributylvinyltin in the presence of lithium chloride and of tetrakis (triphenylphosphine)palladium.

The compounds of formula (II) can be prepared according to the process represented in Appendix 3 by reacting a compound of formula (VIII) with a compound of formula $R_1Y$, in which $R_1$ is defined as in the formula (I) with the exception of hydrogen and Y is a halogen atom, in particular bromine, or a labile group, such as methylsulphonyloxy (mesyloxy) or p-toluenesulphonyloxy (tosyloxy). This reaction can be carried out in the presence of a base, such as potassium carbonate, in a solvent such as acetonitrile. The reaction temperature can be the reflux temperature of the solvent.

The compound of formula (VIII) can be prepared from a compound of formula (IX), where $R_6$ is a protective group for the hydroxyl group, in particular a methyl or phenylmethyl group. To this end, the said protective group $R_6$ is removed by means which are conventional for the person skilled in the art. Thus, when $R_6$ is a methyl group, the compound of formula (IX) is demethylated by means of a Lewis acid, such as boron tribromide, in an organic solvent such as dichloromethane. The temperature employed during this treatment can be between $-20°$ C. and $20°$ C. When $R_6$ is a phenylmethyl group, this protective group can be removed by catalytic hydrogenation. Of course, when the protective group $R_6$ has one of the desired meanings of $R_1$, the compound of formula (IX) can be used directly as compound of formula (II).

The compound of formula (IX) can be prepared by decarboxylation of a compound of formula (X), by heating at a temperature in the region of the melting point of the latter compound, indeed at a temperature greater than the said melting point.

The compound of formula (X) can be prepared by saponification of a compound of formula (XI) by means of a base, such as potassium hydroxide, in alcoholic medium. The saponification reaction can be carried out at a temperature of between $0°$ C. and the reflux temperature of the solvent. In the formula (XI), $R_7$ represents a methyl or ethyl group.

The compound of formula (XI) can be prepared by reacting a compound of formula (XII), where $R_7$ represents a methyl or ethyl group, with ethyl chloroformate. This reaction can be carried out in the presence of a base, such as potassium carbonate, in a solvent such as toluene. This reaction can be carried out at the reflux temperature of the solvent.

In each of the compounds of formulae (VIII), (IX), (X), (XI) and (XII), X has one of the meanings given in the formula (I).

The compounds of formula (XII) can be prepared according to various synthetic routes depending on the nature of X. These synthetic routes are represented in Appendix 4.

The compounds of formula (XII) where X is a sulphur atom and $R_6$ and $R_7$ each represent a methyl group can be prepared by reacting 3-nitro-4-cyanoanisole with methyl thioglycolate. This reaction can be carried out in the presence of a base, such as potassium hydroxide, in a solvent such as N,N-dimethylformamide. This reaction can be carried out at $0°$ C.

3-Nitro-4-cyanoanisole is a known compound. It can be prepared according to the process described by A. H. Cook et al., J. Chem. Soc., 1945, 68, 861.

The compounds of formula (XII) in which X is an oxygen atom or $NR_4$ can be prepared by a process according to which a compound of formula (XIII) is treated either with sodium ethoxide, when X represents an oxygen atom, or with potassium tert-butoxide, when X represents $NR_4$.

The compound of formula (XIII) can be prepared by reacting a compound of formula (XIV), where X is an oxygen atom or $NR_4$, with sodium hydride and then ethyl bromoacetate.

A compound of formula (XIV) where X is an oxygen atom can be prepared by reacting 2-hydroxy-4-(phenylmethoxy)benzaldehyde with nitroethane or hydroxylamine and ethyl formate. 2-Hydroxy-4-(phenylmethoxy) benzaldehyde is a known compound which can be prepared according to J. S. H. Davies (J. Chem. Soc., 1950, 3206).

A compound of formula (XIV) where X is an $NR_4$ group can be prepared by reacting a compound of formula (XV) with a compound of formula $R_4NH_2$, such as methylamine.

The compound of formula (XV) can itself be obtained by reacting commercially available 2-fluoro-4-hydroxybenzonitrile with benzyl bromide. In the compounds of formula (XIV) and $R_4NH_2$, $R_4$ has one of the meanings given for the formula (I).

The 5(R) and 5(S) enantiomers of the compounds of formula (I) are prepared respectively from the (S) and (R) enantiomers of 4-(methoxymethyl)-1,3-dioxolan-2-one of formula (III), according to the process described above.

(S)-4-(Methoxymethyl)-1,3-dioxolan-2-one is a known compound, the preparation of which is described in Patent EP 0,511,031.

(R)-4-(Methoxymethyl)-1,3-dioxolan-2-one is prepared according to the same method, from (R)-2,2-dimethyl-1,3-dioxolane-4-methanol.

The aim of the following examples is to illustrate the preparation of some compounds of the invention. The elemental microanalyses and the N.M.R. spectra confirm the structures of the compounds obtained. In the names of the compounds, the dash "-" forms part of a word and the dash "_" is only used for the break at the line end; it is to be omitted in the absence of a break and must not be replaced either by a normal dash or by a space.

EXAMPLE 1

(R)-5-(Methoxymethyl)-3-[6-(phenylmethoxy) benzofuran3-yl]oxazolidin-2-one 1.1. (R)-4-(Methoxymethyl)-2,2-dimethyl-1,3-dioxolane 420 ml of demineralized water and 420 g (10.5 mol) of sodium hydroxide pellets are introduced into a 6-liter reactor equipped with a reflux condenser, a temperature probe and a dropping funnel. 2.3 l of dichloromethane, 396 g (3.00 mol) of (R)-2,2-dimethyl-1,3-dioxolane-4-methanol ($[\alpha]_D^{20}=-11°$, c=4, methanol) and 20.5 g (0.090 mol) of benzyltriethyl ammonium chloride are added to the stirred solution at $20°$ C. 567 g (4.50 mol) of dimethyl sulphate are then added over 50 min, the temperature being maintained below $30°$ C. The mixture is stirred for 18 hours and then 1 liter of water is added. The organic phase is separated and is washed with 0.5 l of water. The aqueous phases are reextracted with 3 l of dichloromethane and then the organic phases are combined, filtered and concentrated by distillation under reduced pressure. 496 g of product are obtained.

1.2. (S)-3-Methoxypropane-1,2-diol

A mixture of the 496 g of product obtained in the preceding stage in 220 ml of demineralized water is heated to $60°$ C., with stirring, and then 1.5 ml of 36% hydrochloric acid are added. Heating is maintained for 40 min and then the mixture is brought to pH 8–9 by addition of 19 ml of triethylamine. The solvent is evaporated under a pressure of 5.2 kPa, at a temperature of less than $70°$ C., and then the residue is distilled at $61°$ C. under a pressure of 13 Pa. 246 g of product are obtained.

$[\alpha]_D^{20}=+5.8°$ (c=4, methanol).

1.3. (R)-4-(Methoxymethyl)-1,3-dioxolan-2-one 245 g (3.31 mol) of (S)-3-methoxypropane-1,2-diol and 560 ml (4.62 mol) of diethyl carbonate are introduced into a round-bottomed flask equipped with a dropping funnel and a distillation assembly. The mixture is heated to $95°$ C. and then a sodium methoxide solution, obtained from 10 ml of methanol and 0.5 g (0.02 mol) of sodium, is added. The ethanol formed during the reaction is distilled off over 2 hours (vessel temperature: 95 to $112°$ C.; column temperature: 82 to $78°$ C.) and the mixture is then cooled and distilled under a pressure of 13 Pa in order to separate off the excess diethyl carbonate. 267 g of product are obtained.

$[\alpha]_D^{20}=+30.3°$ (c=1, dichloromethane).

1.4. 2-Hydroxy-4-(phenylmethoxy)benzonitrile

A mixture of 226 g (1.00 mol) of 2-hydroxy-4 (phenylmethoxy)benzaldehyde in 287 ml (3.83 mol) of nitroethane and of 313 g (2.3 mol) of sodium acetate in 570 ml of acetic acid is heated at 104° C. for 8 hours and is then poured into 3 l of a mixture of water and ice. The precipitate is then filtered off, rinsed with diisopropyl ether and dried. 118 g of product are obtained. Moreover, the filtrate is extracted with diethyl ether, the organic phase is washed with an aqueous sodium hydrogencarbonate solution and then with water, dried over sodium sulphate and concentrated under reduced pressure and the residue is then triturated in diisopropyl ether. 67 additional g of product are thus obtained.

Melting point: 130° C.

1.5. Ethyl 2-cyano-5-(phenylmethoxy)phenoxyacetate 9.7 g (0.20 mol) of 50% sodium hydride are slowly added portionwise to a solution of 46 g (0.20 mol) of 2-hydroxy-4-(phenylmethoxy)benzonitrile in a mixture of 450 ml of tetrahydrofuran and 450 ml of dimethylformamide. The mixture is stirred for 30 minutes and then 22.4 ml (0.20 mol) of ethyl bromoacetate are added dropwise. Reaction is allowed to take place for 30 minutes, the reaction mixture is then poured into ice-cold water and the product is extracted with ethyl acetate. The organic phase is then washed with water, dried over sodium sulphate and concentrated under reduced pressure. After trituration of the residue in diisopropyl ether, 50 g of product are obtained.

Melting point: 84° C.

1.6. Ethyl 3-amino-6-(phenylmethoxy)benzofuran-2-carboxylate 50 g (0.16 mol) of ethyl 2-cyano-5-(phenylmethoxy) phenoxyacetate are added protionwise to a sodium ethoxide solution obtained from 1.8 g (0.080 mol) of sodium and 400 ml of ethanol. The mixture is heated for 1 hour at reflux and is then poured into water and the product is extracted with ethyl acetate. The organic phase is then washed with a saturated aqueous sodium chloride solution and is then dried over sodium sulphate and concentrated under reduced pressure. After purification by chromatography on a silica column with dichloromethane, 40 g of product are obtained.

Melting point: 95° C.

1.7. Ethyl 3-[(ethoxycarbonyl)amino]-6-(phenylmethoxy) benzofuran-2-carboxylate A mixture of 40 g (0.13 mol) of ethyl 3-amino-6-(phenylmethoxy)benzofuran-2-carboxylate, 18 ml (0.19 mol) of ethyl chloroformate and 51 g (0.37 mol) of potassium carbonate in 400 ml of benzene is heated at reflux for 18 hours and is then cooled and filtered and the filtrate is concentrated under reduced pressure. 41 g of product are obtained by recrystallization of the residue from diisopropyl ether.

Melting point: 100° C.

1.8. 3-[(Ethoxycarbonyl)amino]-6-(phenylmethoxy) benzofuran-2-carboxylic acid 200 ml of a 10% ethanolic potassium hydroxide solution are added to a solution of 41 g (0.11 mmol) of ethyl 3-[(ethoxycarbonyl)amino]-6-(phenylmethoxy)benzofuran-2-carboxylate in 400 ml of ethanol. The mixture is heated at reflux for 30 minutes and the solvent is then evaporated under reduced pressure. The residue is taken up in water and the solution is acidified with hydrochloric acid to pH 2. 41 g of product are obtained by filtration of the precipitate formed.

Melting point: 198° C.

1.9. Ethyl [6-(phenylmethoxy)benzofuran-3-yl]carbamate

A reactor containing 38.6 g (0.11 mol) of 3-[(ethoxycarbonyl)amino]-6-(phenylmethoxy)benzofuran-2-carboxylic acid under nitrogen is immersed in an oil bath at 185–190° C. for 5 minutes. The residue is then taken up in ethyl acetate and the solution is then washed with an aqueous potassium hydrogencarbonate solution and then with a saturated aqueous sodium chloride solution. The organic phase is then dried over sodium sulphate, the solvent is evaporated and the residue is purified on a silica column with a mixture containing 20% of ethyl acetate in cyclohexane. After trituration in diisopropyl ether, 25 g of product are obtained.

Melting point: 140° C.

1.10. (R)-5-(Methoxymethyl)-3-[6-(phenylmethoxy) benzofuran-3-yl]oxazolidin-2-one A mixture of 85 mg (0.6 mmol) of dry potassium carbonate in 40 ml of anhydrous dimethylformamide is heated to 140° C. and then 1.6 g (12 mmol) of (S)-4-methoxymethyl-1,3-dioxolan-2-one and a solution of 2.0 g (6.4 mmol) of ethyl [6-(phenylmethoxy)benzofuran-3-yl]carbamate in 10 ml of dimethylformamide are successively added. The mixture is stirred for 3 and a half hours at 140° C. and is then poured into ice-cold water. The product is then extracted with ethyl acetate and the organic phase is washed with water, dried over sodium sulphate and concentrated under reduced pressure. The residue is purified by chromatography on a silica column with a mixture containing 30% of ethyl acetate in cyclohexane and then with a mixture containing 2% of ethyl acetate in dichloromethane. After trituration in diisopropyl ether, 1.2 g of product are obtained.

Melting point: 112.6–112.8° C.

$[\alpha]_D^{20}$=−34° C. (c=1, dichloromethane).

(S)-5-(Methoxymethyl)-3-[6-(phenylmethoxy) benzofuran-3-yl]oxazolidin-2-one was obtained from ethyl [6-(phenylmethoxy)benzofuran-3-yl]carbamate and (R)-4-methoxymethyl-1,3-dioxolan-2-one according to the same process.

Melting point: 111.9° C.

$[\alpha]_D^{20}$=+33.3° C. (c=1, dichloromethane).

EXAMPLE 2

(R)-5-(Methoxymethyl)-3-(6-hydroxybenzofuran-3-yl)oxazolidin-2-one 1.4 ml (11 mmol) of dimethylphenylamine and 1.9 g (15 mmol) of aluminium chloride are added to a solution of 1.3 g (3.7 mmol) of (R)-5-(methoxymethyl)-3-[6-(phenylmethoxy)benzofuran-3-yl]oxazolidin-2-one in 50 ml of dichloromethane cooled to 0° C. The mixture is stirred for 1 hour, until room temperature is reached, and is then poured into water and the product is extracted with dichloromethane. The organic phase is then washed with water, dried over sodium sulphate and concentrated under reduced pressure. After trituration of the residue in a mixture of diisopropyl ether and petroleum ether, 0.64 g of product is obtained.

Melting point: 136.0–136.5° C.

$[\alpha]_D^{20}$=−55.3° (c=1, methanol).

(S)-5-(Methoxymethyl)-3-(6-hydroxybenzofuran-3-yl) oxazolidin-2-one was obtained from (S)-5-(methoxymethyl)-3-[6-(phenylmethoxy)benzofuran-3-yl] oxazolidin-2-one according to the same process.

Melting point: 141.2° C.

$[\alpha]_D^{20}$=+50.5° (c=1, methanol).

EXAMPLE 3

(R)-5-(Hydroxymethyl)-3-(6-hydroxybenzofuran-3-yl)oxazolidin-2-one 17 ml of a 1M solution of boron tribromide in dichloromethane are added to a solution of 1.5 g (5.7 mol) of (R)-5-(methoxymethyl)-3-(6-hydroxybenzofuran-3-yl) oxazolidin-2-one in 100 ml of dichloromethane cooled to 0° C. The reaction mixture is stirred for 2 hours and is then poured into an aqueous ammonia solution. The product is then extracted with dichloromethane and the organic phase is then washed with water, dried over sodium sulphate and concentrated under reduced pressure. After chromatography of the residue on a silica column with a mixture containing 4% of methanol in dichloromethane and trituration in diethyl ether, 0.80 g of product is obtained.

Melting point: 172.1–172.2° C.

$[\alpha]_D^{20}$=−39.3° (c=1, dimethyl sulphoxide).

EXAMPLE 4

(R)-5-(Hydroxymethyl)-3-[6-(4,4,4-trifluorobutoxy) benzofuran-3-yl]oxazolidin-2-one A mixture of 0.30 g (1.2 mol) of (R)-5-(hydroxymethyl)-3-(6 -hydroxybenzofuran-3 -yl)oxazolidin-2-one, 0.30 g (1.6 mol) of 1-bromo-4,4,4-trifluorobutane and 0.33 g (2.4 mol) of potassium carbonate in 10 ml of a 2/8 mixture of dimethylformamide and acetonitrile is stirred at 80° C. for 2 hours and is then filtered and the solvent is evaporated under reduced pressure. The residue is then taken up in ethyl acetate and the organic phase is then washed with water, dried over sodium sulphate and concentrated under reduced pressure. After recrystallization from isopropyl alcohol, 0.30 g of product is obtained.

Melting point: 194.0° C.

$[\alpha]_D^{20}$ =−26.7° (c =1, dimethyl sulphoxide).

EXAMPLE 5

(R,R)-5-(Methoxymethyl)-3-[6-(4,4,4-trifluoro-3-hydroxybutoxy)benzofuran-3-yl]oxazolidin-2-one A mixture of 0.43 g (1.6 mmol) of (R)-5-(methoxymethyl)-3-(6-hydroxybenzofuran-3-yl) oxazolidin-2-one, 0.63 g (2.1 mmol) of (R)-4,4,4-trifluoro-3-hydroxybutyl tosylate and 0.45 g (3.6 mmol) of potassium carbonate in 40 ml of acetonitrile is stirred at reflux for 2 hours and is then filtered and the filtrate is concentrated under reduced pressure. The residue is taken up in ethyl acetate and the organic phase is then washed with water, dried over sodium sulphate and concentrated under reduced pressure. The residue is purified by chromatography on a silica column with a mixture containing 50% of ethyl acetate in cyclohexane. 0.52 g of product is obtained by crystallization from a mixture of diethyl ether and hexane.

Melting point: 80.5–82.0° C.

$[\alpha]_D^{20}$5.3° (c =1, dichloromethane).

(S,R)-5-(Methoxymethyl)-3-[6-(4,4,4-trifluoro-3-hydroxybutoxy)benzofuran-3-yl]oxazolidin-2-one was obtained from (S)-5-(methoxymethyl)-3-(6-hydroxybenzofuran-3-yl)oxazolidin-2-one and (R)-4,4,4-trifluoro-3-hydroxybutyl tosylate according to the same process.

Melting point: 119.6–119.7° C.

$[\alpha]_D^{20}$=+50.8° (c=1, dichloromethane).

EXAMPLE 6

(S,R)-5-(Hydroxymethyl)-3-[6-(4,4,4-trifluoro-3-hydroxybutoxy)benzofuran-3-yl]oxazolidin-2-one 0.8 ml of a 1M solution of boron tribromide in dichloromethane is added to a solution of 100 mg (0.26 mmol) of (S,R)-5-(methoxymethyl)-3-[6-(4,4,4-trifluoro-3-hydroxybutoxy)benzofuran-3-yl]oxazolidin-2-one in 8 ml of dichloromethane cooled to 0° C. The reaction mixture is stirred for 2 hours and is then poured into an ice-cold aqueous ammonia solution. The product is then extracted with dichloromethane and the organic phase is washed with water, dried over sodium sulphate and concentrated under reduced pressure. After chromatography of the residue on a silica column with a mixture containing 70% of ethyl acetate in cyclohexane, 50 mg of product are obtained.

Melting point: 163.9–164.0° C.

$[\alpha]_D^{20}$=+57.9° (c=1, dimethyl sulphoxide).

EXAMPLE 7

(R)-5-(Methoxymethyl)-3-[6-(cyclopropylmethoxy) benzofuran-3-yl]oxazolidin-2-one 0.50 g (3.6 mmol) of potassium carbonate and 0.20 ml (2.1 mmol) of bromomethylcyclopropane are added to a solution of 0.47 g (1.8 mmol) of (R)-5-(methoxymethyl)3-(6-hydroxybenzofuran-3-yl)oxazolidin-2-one in 40 ml of acetonitrile. The reaction mixture is heated at 50–60° C. for 24 hours and is then filtered and the solvent is evaporated under reduced pressure. The residue is taken up in dichloromethane, the organic phase is then washed with water and dried and the solvent is evaporated. After chromatography of the residue on a silica column with a mixture containing 40% of ethyl acetate in cyclohexane and recrystallizing twice from isopropyl alcohol, 0.39 g of product is obtained.

Melting point: 139.9–140.0° C.

$[\alpha]_D^{20}$=−39.2° (c=1, dichloromethane).

EXAMPLE 8

(R,R)-5-(Methoxymethyl)-3-[6-(5,5,5-trifluoro-4-hydroxypent-1-enyl)benzofuran-3-yl]oxazolidin-2-one 8.1. (R)-3-[5-(Methoxymethyl)-2-oxooxazolidin-3yl] benzofuran-6-yl trifluoromethanesulphonate 5.8 ml (0.035 mol) of trifluoromethanesulphonic anhydride are added slowly to a solution, maintained at −20° C., of 7.6 g (0.029 mol) of (R)-5-(methoxymethyl)-3-(6-hydroxybenzofuran-3-yl)oxazolidin-2-one in 60 ml of pyridine. After returning to room temperature, the mixture is poured into ice and is brought to a pH of 6 by means of 2N hydrochloric acid. The product is then extracted with ethyl acetate, the solvent is evaporated under reduced pressure and the product is purified by chromatography on silica gel with a 10/90 mixture of cyclohexane and dichloromethane.

10.2 g of product are recovered. Melting point: 98° C.

8.2. Methyl (R)-3-[5-(methoxymethyl)-2-oxooxazolidin-3-yl]benzofuran-6-carboxylate 0.26 g (0.001 mol) of palladium acetate, 12 ml (0.086 mol) of triethylamine, 86 ml of methanol and 0.48 g (0.001 mol) of bis(diphenylphosphino)propane are added to a solution of 15.4 g (0.033 mol) of (R)-3-[5-(methoxymethyl)-2-oxooxazolidin-3-yl]benzofuran-6-yl trifluoromethanesulphonate in 234 ml of dimethyl sulphoxide. The mixture is placed under a carbon monoxide atmosphere and is heated for three hours. The mixture is then filtered through celite, the filtrate is taken up in ethyl ether, washed with water and dried over sodium sulphate and the aqueous phase is evaporated under reduced pressure. The product is purified by chromatography on silica gel with a 99/1 mixture of dichloromethane and methanol. 5.3 g of product are recovered. Melting point: 116° C.

8.3. (R)-3-[6-(Hydroxymethyl)benzofuran-3-yl]-5-(methoxymethyl)oxazolidin-2-one 22 ml of a 2M solution (0.044 mol) of a borane-dimethyl sulphide complex in tetrahydrofuran are added, in two steps, to a solution of 3.3 g (0.011 mol) of methyl (R)-3-[5-(methoxymethyl)-2-oxooxazolidin-3-yl]benzofuran-6-carboxylate in 40 ml of tetrahydrofuran and the mixture is heated for five hours at 55° C. The mixture is hydrolysed with 1N hydrochloric acid. The mixture is poured into water and the product is extracted with dichloromethane. The organic phase is dried over sodium sulphate and concentrated under reduced pressure. The product is purified by chromatography on silica gel with a 99/1 mixture of dichloromethane and methanol. After crystallization from ethyl ether, 2.0 g of product are recovered.

Melting point: 112° C.

8.4. (R)-3-(6-Formylbenzofuran-3-yl)-5-(methoxymethyl)oxazolidin-2-one 1 ml (14.4 mmol) of dimethyl sulphoxide in 20 ml of dichloromethane is added to a solution, cooled to −70° C., of 0.75 ml (8.6 mmol) of oxalyl chloride in 20 ml of dichloromethane. The mixture is stirred for 15 min and a solution of 2.0 g (7.2 mmol) of (R)-3-[6-(hydroxymethyl)benzofuran-3-yl]-5-(methoxymethyl)oxazolidin-2-one in 35 ml of dichloromethane is slowly added. The mixture is stirred for three hours at −70° C. and 5.0 ml (36 mmol) of triethylamine are added. After returning to room temperature, the mixture is poured into 50 ml of water, the product is extracted with dichloromethane and the organic phase is dried over sodium sulphate and concentrated under reduced pressure. The product is purified by chromatography on silica gel and an oil is recovered which is crystallized from ethyl ether.

1.1 g of product are obtained. Melting point: 94–95° C.

8.5. (R,R)-5-(Methoxymethyl)-3-[6-(5,5,5-trifluoro-4-hydroxypent-1-enyl)benzofuran-3-yl]oxazolidin-2-one A mixture comprising 0.23 g (0.8 mmol) of (R)-3-(6-formylbenzofuran-3-yl)-5-(methoxymethyl)oxazolidin-2-one, 0.50 g (1.0 mmol) of (3-hydroxy-4,4,4-trifluorobutyl)triphenylphosphonium bromide, 0.16 g (1.2 mmol) of potassium carbonate in 2.5 ml of dioxane and 0.17 ml of formamide is heated for 24 hours at 80° C. The mixture is then poured into water, the product is extracted with ethyl acetate and the organic phase is dried over sodium sulphate and concentrated under reduced pressure. The product is purified by chromatography on silica gel with a 95/5 mixture of dichloromethane and ethyl acetate. After trituration in diisopropyl ether, 0.10 g of pure trans isomer is recovered. Melting point: 116.5–116.8° C.

$[\alpha]_D^{20}$=−15.1° (c=1, dichloromethane).

EXAMPLE 9

(R,R)-5-(Methoxymethyl)-3-[6-(5,5,5-trifluoro-4-hydroxypentyl)benzofuran-3-yl]oxazolidin-2-one 0.05 g of palladium-on-charcoal is added to a solution in 8.5 ml of ethanol of 0.26 g (0.67 mmol) of (R,R)-5-(methoxymethyl)-3-[6-(5,5,5-trifluoro-4-hydroxypent-1-enyl)benzofuran-3-yl]oxazolidin-2-one obtained in Example 8. The mixture is placed under a hydrogen atmosphere for 18 hours, the palladium-on-charcoal is removed by filtration and the filtrate is concentrated under reduced pressure. The product is then purifiedtran by chromatography on silica gel with a 60/40 mixture of cyclohexane and ethyl acetate. 0.14 g of product is recovered after crystallization from diisopropyl ether.

Melting point: 85.8–86.2° C.

$[\alpha]_D^{20}$=−18.0° (c=1, dicholoromethane).

EXAMPLE 10

(R)-5-(Methoxymethyl)-3-[6-(5,5,5-trifluoropent-1-enyl)benzofuran-3-yl]oxazolidin-2-one A mixture comprising 0.30 g (1.1 mmol) of (R)-3-(6-formylbenzofuran-3-yl)-5-(methoxymethyl)oxazolidin-2-one, 0.59 g (1.3 mmol) of (4,4,4-trifluorobutyl)triphenylphosphonium bromide, 0.21 g (1.5 mmol) of potassium carbonate in 3.5 ml of dioxane and 0.22 ml of formamide is heated for six hours at reflux. The mixture is then poured into water, the product is extracted with ethyl acetate and the organic phase is dried over sodium sulphate and concentrated under reduced pressure. The product is purified by chromatography on silica gel with a 99.5/0.5 mixture of dichloromethane and ethyl acetate. The product is crystallized from petroleum ether and 0.35 g thereof is recovered in the form of a 67/33 cis/trans mixture.

Melting point: 57–63° C.

$[\alpha]_D^{20}$=−36.3° (c=1, dichloromethane).

EXAMPLE 11

(R)-5-(Methoxymethyl)-3-[6-(5,5,5-trifluoropentyl)benzofuran-3-yl]oxazolidin-2-one 0.03 g of palladium-on-charcoal is added to a solution in 5 ml of ethanol of 0.13 g (0.35 mmol) of the cis/trans mixture of (R)-5-(methoxymethyl)-3-[6-(5,5,5-trifluoropent-1-enyl)benzofuran-3-yl]oxazolidin-2-one obtained in Example 10. The mixture is placed under a hydrogen atmosphere for eight hours, the palladium-on-charcoal is then removed by filtration and the filtrate is concentrated under reduced pressure. The product is then purified by chromatography on silica gel with a 99.5/0.5 mixture of dichloromethane and methanol. 0.1 g of product is recovered.

Melting point: 65.7–65.9° C.

$[\alpha]_D^{20}$=−31.6° (c=1, dichloromethane).

EXAMPLE 12

(R)-3-(6-Ethenylbenzofuran-3-yl)-5-(methoxymethyl) oxazolidin-2-one

A mixture of 3.6 g (9.1 mmol) of (R)-3-[5-(methoxymethyl)-2-oxooxazolidin-3-yl]benzofuran-6-yl trifluoromethanesulphonate, 1.1 g (27.3 mol) of lithium chloride, 2.9 g (9.1 mmol) tributylvinyltin and 0.18 g (0.15 mmol) of tetrakis(triphenylphosphine)palladium in 40 ml of dioxane is heated at 101° C. The solvent is then evaporated under reduced pressure, the residue is taken up in ethyl acetate and the organic phase is washed with water, dried over sodium sulphate and concentrated under reduced pressure. The residue is purified by chromatography on silica gel with a 70/30 mixture of cyclohexane and ethyl acetate. 1.9 g of product are recovered.

Melting point: 89.0–89.1° C.

$[\alpha]_D^{20}$=−49.4° (c=1, dichloromethane).

EXAMPLE 13

(R)-5-(Methoxymethyl)-3-[6-(phenylmethoxy)benzo
[b] thien-3-yl]oxazolidin-2-one 13.1. Methyl 3-amino-6-methoxybenzo[b]thiophene-2-carboxylate A solution of 20.3 g (0.363 mol) of potassium hydroxide in 100 ml of water is added to a mixture of 36.3 g (0.204 mol) of 3-nitro-4-cyanoanisole and 26 g (0.245 mol) of methyl thioglycolate in 400 ml of N,N-d-methylformamide, the temperature being maintained at 0° C. The mixture is left stirring at 0° C. for 20 min and is then poured into a mixture of water and ice. The precipitate is then filtered off, rinsed with water and dried. The product is dissolved in a mixture of dichloromethane and tetrahydrofuran, the organic phase is then dried over sodium sulphate and concentrated under reduced pressure and the residue is triturated in dichloromethane. 26.2 g of product are thus obtained in the form of a light-beige powder.

Melting point: 170° C.

13.2. Methyl 3-[(ethoxycarbonyl)amino]-6-methoxybenzo[b]thiophene-2-carboxylate

A mixture of 27.4 g (0.115 mol) of methyl 3-amino-6-methoxybenzo[b]thiophene-2-carboxylate, 38 g (0.275 mol) of potassium carbonate and 13.2 ml (0.138 mol) of ethyl chloroformate in 330 ml of toluene is heated at reflux for three hours. 7 ml (0.069 mol) of ethyl chloroformate are then added and the mixture is left heating at reflux for a further seven hours, with stirring. The mixture is then diluted with dichloromethane and washed with water. The organic phase is dried over sodium sulphate and the solvent is evaporated under reduced pressure. Recrystallization is carried out from a mixture of isopropanol and diisopropyl ether. 31.2 g of product are obtained.

Melting point: 137° C.

13.3. 3-[(Ethoxycarbonyl)amino]-6-methoxybenzo[b]thiophene-2-carboxylic acid 92 ml of a 10% ethanolic potassium hydroxide solution are added to a solution of 31.4 g (0.101 mol) of methyl 3-[(ethoxycarbonyl)amino]-6-methoxybenzo[b]thiophene-2-carboxylate in 230 ml of ethanol. The mixture is heated at 60° C. for 10 minutes and is then poured onto ice-cold water. The mixture is acidified by addition of a 6N hydrochloric acid solution and the precipitate formed is filtered off, rinsed with water and dried under reduced pressure. The solid is triturated in ethanol. 22.8 g of product are recovered.

Melting point: 260° C.

13.4. Ethyl (6-methoxybenzo[b]thien-3-yl)carbamate 11.4 g of 3-[(ethoxycarbonyl)amino]-6-methoxybenzo[b]thiophene-2-carboxylic acid are heated at 220–225° C. A vitreous gum is obtained which is taken up in tetrahydrofuran until dissolved. The solvent is evaporated under reduced pressure and the residue is purified on a silica column with a 10/90 mixture of ethyl acetate and cyclohexane. 19.4 g of product are obtained.

Melting point: 88° C.

13.5. Ethyl (6-hydroxybenzo [b]thien-3-yl)carbamate 46 ml of a 1M solution of boron tribromide (0.046 mol) in dichloromethane are added to a solution of 7.7 g (0.031 mol) of ethyl (6-methoxybenzo[b]thien-3-yl)carbamate in 80 ml of dichloromethane, while maintaining the temperature at 0° C. The mixture is allowed to return to room temperature and 15 ml of a 1M solution of boron tribromide (0.015 mol) in dichloromethane are added. The mixture is stirred for 180 min, neutralization is then carried out with a dilute ammonium hydroxide solution and the precipitate obtained is filtered off. The latter is washed with water and dried. Purification is carried out by chromatography on a column of silica gel with dichloromethane. 6 g of product are obtained.

Melting point: 159–160° C.

13.6. Ethyl [6-(phenylmethoxy)benzo[b]thien-3-yl] carbamate

A mixture comprising 2 g (8.4 mmol) of ethyl (6-hydroxybenzo[b]thien-3-yl)carbamate, 2.16 g (12.6 mmol) of benzyl bromide and 2.3 g (16.8 mmol) of potassium carbonate in 30 ml of acetonitrile is heated at reflux for 11 hours. The mixture is filtered, the solvent is evaporated under reduced pressure and the residue is triturated in petroleum ether. 2.3 g of product are obtained.

Melting point: 129–130° C.

13.7. (R)-5-(Methoxymethyl)-3-[6-(phenylmethoxy)benzo [b]thien-3-yl]oxazolidin-2-one A mixture comprising 1.1 g (3.36 mmol) of ethyl [6-(phenylmethoxy)benzo[b]thien-3-yl]carbamate, 0.58 g (4.4 mmol) of (S)-4-(methoxymethyl)-1,3-dioxolan-2-one and 46 mg (0.34 mmol) of potassium carbonate in 16 ml of N,N-dimethylformamide is brought to 140° C. After 30 min at 140° C., 0.3 g (2 mmol) of (S)-4-(methoxymethyl)-1,3-dioxolan-2-one is added. The mixture is left at this temperature for a further 210 min, is poured into ice-cold water and the product is then extracted with dichloromethane. The solvent is removed under reduced pressure and purification is carried out by chromatography on a column of silica gel with an 80/20 mixture of cyclohexane and ethyl acetate. 0.15 g of product is obtained in the form of an oil.

$[\alpha]_D^{20}=-18.9°$ (c=1, dichloromethane).

EXAMPLE 14

(R)-5-(Methoxymethyl)-3-[6-(4,4.4-trifluorobutoxy)
benzo[b]thien-3-yl]oxazolidin-2-one 14.1. Ethyl [6-(4,4,4-trifluorobutoxy)benzo[b]thien-3-yl] carbamate A mixture of 2.0 g (8.4 mmol) of ethyl 6-hydroxybenzothiophene-3-carbamate (obtained in Stage 13.5. of Example 13), 2.4 g (12.6 mmol) of 4,4,4-trifluoro-1-bromobutane and 2.3 g (16.8 mmol) of potassium carbonate in 30 ml of acetonitrile is heated at reflux for 90 min. The mixture is evaporated under reduced pressure and the residue is triturated in petroleum ether. 2.65 g of product are obtained.

Melting point: 103° C.

14.2. (R)-5-(Methoxymethyl)-3-[6-(4,4,4-trifluorobutoxy) benzo[b] thien-3-yl] oxazolidin-2-one A mixture comprising 1.3 g (3.74 mol) of ethyl [6-(4,4,4-trifluorobutoxy)benzo[b]thien-3-yl]carbamate, 0.64 g (4.8 mmol) of (S)-4-(methoxymethyl)-1,3-dioxolan-2-one and 50 mg (0.36 mmol) of potassium carbonate in 16 ml of N,N-dimethylformamide is heated at 140° C. for five hours. The solvent is evaporated under reduced pressure and the oil obtained is purified by chromatography on a column of silica gel with an 80/20 mixture of cyclohexane and ethyl acetate. 0.4 g of product is recovered in the form of an oil.

$[\alpha]_D^{20}=-21.8°$ (c=1, dichloromethane).

EXAMPLE 15

(R,R)-5-(Methoxymethyl)-3-[6-(4,4,4-trifluoro-3-hydroxybutoxy)benzo [b] thien-3-yl]oxazolidin-2-one 15.1 Ethyl (R)-3-[[(1,1-dimethylethyl)dimethylsilyl]oxy]-4, 4, 4-trifluorobutanoate 8.36 g (0.123 mol) of imidazole and then 13.5 g (0.09 mol) of t-butyldimethylsilyl chloride are added to a solution of 15.2 g (0.082 mol) of ethyl (R)-4,4,4-trifluoro-3-hydroxybutanoate in 75 ml of N,N-dimethylformamide. The mixture is poured onto 380 ml of water, the product is extracted with dichloromethane and the organic phase is washed with two times 150 ml of water. The product is dried and the solvent is evaporated under reduced pressure. Purification is carried out by chromatography on a column of silica gel with a 95/5 mixture of cyclohexane and ethyl acetate. 20.3 g of a colourless oil are obtained.

$[\alpha]_D^{20}$=+32.4° (c=1, methanol).

15.2. (R)-3-[[(1,1-Dimethylethyl)dimethylsilyl]oxy]-4,4,4-trifluorobutanol 224 ml (0.224 mol) of a 1M diisobutyl aluminium hydride solution are added to a solution, cooled to −50° C., of 22.4 g (0.0745 mol) of ethyl (R)-3-[[(1,1-dimethylethyl)dimethylsilyl]oxy]-4,4,4-trifluorobutanoate in 224 ml of dichloromethane. The mixture is allowed to return to room temperature and 15 ml of methanol are added, at −50° C. The mixture is then poured onto a mixture of 1N hydrochloric acid and ice and the product is then extracted with dichloromethane. The organic phase is dried over sodium sulphate and the solvent is evaporated under reduced pressure. 15.6 g of a pale-yellow oil are obtained.

$[\alpha]_D^{20}$=+25.9° (c=1, methanol).

15.3. (R)-3-[[(1,1-Dimethylethyl)dimethylsilyl]oxy]-4,4,4-trifluorobutyl 4-methylbenzenesulphonate 11 mg of dimethylaminopyridine are added to a solution of 15.1 g (0.058 mol) of (R)-3-[[(1,1-dimethylethyl)dimethylsilyl]oxy]-4,4,4-trifluorobutanol in a mixture of 9.4 ml (0.117 mol) of pyridine and 35 ml of dichloroethane. The mixture is cooled to 0° C. and a solution of 11.4 g (0.06 mol) of p-methylbenzenesulphonyl chloride in 15 ml of dichloroethane is added. The mixture is left stirring for 48 hours at room temperature. The mixture is poured onto ice-cold water, the product is extracted with dichloromethane, the organic phase is washed with water and dried over sodium sulphate and the solvent is evaporated under reduced pressure. A yellow oil is recovered which is purified by chromatography on a column of silica gel with an 80/20 mixture of cyclohexane and dichloromethane. 14.9 g of a colourless oil are obtained.

$[\alpha]_D^{20}$=+15.7° (c=1, dichloromethane).

15.4. Ethyl (R)-(6-(3-([[(1,1-dimethylethyl)dimethylsilyl]oxy]-4, 4,4-trifluorobutoxy]benzo[b]thien-3-yl) carbamate A mixture of 0.3 g (1.26 mmol) of ethyl (6-hydroxybenzo[b]thien-3-yl)carbamate, 0.62 g (1.52 mmol) of (R)-3-[[(1,1-dimethylethyl)dimethylsilyl]oxy]-4,4,4-trifluorobutyl 4-methylbenzenesulphonate and 0.34 g (2.52 mmol) of potassium carbonate in 5 ml of acetonitrile is heated at reflux for four hours. The mixture is filtered, the solvent is evaporated under reduced pressure, the product is taken up in dichloromethane, the organic phase is washed with water and dried over sodium sulphate and the solvent is evaporated under reduced pressure. The product is purified by chromatography on a column of silica gel with a 90/10 mixture of cyclohexane and ethyl acetate. 518 mg of a yellow oil are obtained.

15.5. (R,R)-5-(Methoxymethyl)-3-[6-(4,4,4-trifluoro-3-hydroxybutoxy)benzo[b]thien-3-yl]oxazolidin-2-one A mixture of 1.5 g (0.00314 mol) of ethyl (R)-[6-[3-[[(1,1-dimethylethyl)dimethylsilyl]oxy]- 4,4,4-trifluorobutoxy]benzo[b]thien-3-yl]carbamate, 0.415 g (0.00314 mol) of (S)-4-(methoxymethyl)-1,3-dioxolan-2-one and 43 mg (0.00031 mol) of potassium carbonate in 15 ml of N,N-dimethylformamide is heated at 140° C. for 10 hours. Heating is then carried out for an additional ten hours at 140° C. while adding, in two steps, 0.041 g (0.00031 mol) of (S)-4-(methoxymethyl)-1,3-dioxolan-2-one. The solvent is evaporated under reduced pressure, the product is taken up in dichloromethane, the organic phase is washed with an aqueous sodium chloride solution and dried over sodium sulphate and the solvent is evaporated under reduced pressure. The product thus obtained is mixed with 297 mg (0.14 mmol) of tetra-n-butylammonium fluoride in 15 ml of tetrahydrofuran. The mixture is stirred at room temperature overnight, the solvent is evaporated under reduced pressure and the product is purified by chromatography on a column of silica gel with a 70/30 mixture of cyclohexane and ethyl acetate. 150 mg of product are obtained in the form of a yellow oil.

$[\alpha]_D^{20}$=−1.8° (c=1, dichloromethane).

EXAMPLE 16

(R)-5-(Hydroxymethyl)-3-[6-(4,4,4-trifluorobutoxy) benzo[b]thien-3-yl]oxazolidin-2-one 2.3 ml of a 1M solution of boron tribromide (2.3 mmol) in dichloromethane are added to a solution comprising 0.3 g (0.77 mmol) of (R)-5-(methoxymethyl)-3-[6-(4,4,4-trifluorobutoxy)benzo[b]thien-3-yl]oxazolidin-2-one in 3 ml of dichloromethane, cooled to 0° C. After 150 min, the mixture is basified with ammonium hydroxide, while maintaining the temperature at 0° C. The mixture is left stirring for 30 min, the product is extracted with dichloromethane, the organic phase is washed with water and dried over sodium sulphate and the solvent is evaporated under reduced pressure. Purification is carried out by chromatography on a column of silica gel with a 40/60 mixture of cyclohexane and ethyl acetate. 289 mg of product are obtained.

Melting point: 107.0–107.2° C.

$[\alpha]_D^{20}$=−20.5° (c=1, dichloromethane).

EXAMPLE 17

(R)-5-(Methoxymethyl)-3-[1-methyl-6-(phenylmethoxy)-1H-indol-3-yl]oxazolidin-2-one 17.1. 2-Fluoro-4-(phenylmethoxy)benzonitrile A mixture of 40.8 g (0.297 mol) of 2-fluoro-4-hydroxybenzonitrile, 61.06 g (0.357 mol) of benzyl bromide and 82 g (0.594 mol) of potassium carbonate in 400 ml of acetonitrile is brought to the reflux temperature for two hours. The mixture is filtered, the solvent is evaporated under reduced pressure and the evaporation residue is triturated with diisopropyl ether. 65.5 g of product are recovered.

Melting point: 87° C.

17.2. 2-(Methylamino)-4-(phenylmethoxy)benzonitrile

A solution of 32 g (0.14 mol) of 2-fluoro-4-(phenylmethoxy)benzontirile and of 35 ml of methylamine in 150 ml of ethanol is heated for 32 hours at 80° C. The reaction mixture is taken up in dichloromethane and the organic phase is washed three times with water and dried over sodium sulphate. The solvent is then evaporated under reduced pressure and 32.9 g of product are recovered.

Melting point: 120° C.

17.3. Ethyl [[2-cyano-5-(phenylmethoxy)phenyl]methylamino]acetate 64.1 g (0.269 mol) of 2-(methylamino)-4-(phenylmethoxy)benzonitrile in 393 ml of ethanol are added to a solution of 39.3 g (0.285 mol) of potassium carbonate in 393 ml of water. 152.8 g (0.914 mol) of ethyl bromoacetate are then added and the mixture is brought to reflux. After 48 hours, the ethanol is evaporated under reduced pressure, the residue is taken up in dichloromethane and the organic phase is washed with water and dried over sodium sulphate. The solvent is evaporated under reduced pressure and the residue is purified by chromatography on silica gel, elution being carried out with dichloromethane. 19.5 g of product are recovered, which product exists in the form of an oil.

17.4. Ethyl 3-amino-1-methyl-6-(phenylmethoxy)-1H-indole-2-carboxylate

A solution of 28.3 g (0.087 mol) of ethyl ([2-cyano-5-(phenylmethoxy)phenyl]methylamino]acetate, in solution in 80 ml of tetrahydrofuran, is slowly added to a suspension of 9.8 g (0.087 mol) of potassium tert-butoxide in 100 ml of tetrahydrofuran, the temperature being maintained at less than 30° C. The mixture is left stirring at room temperature for 25 min and is then poured onto a mixture of water and ice. The product is extracted with dichloromethane, the organic phase is washed with water and the solvent is evaporated under reduced pressure. The residue thus obtained is triturated in ethanol and 22.6 g of product are recovered.

Melting point: 95° C.

17.5. Ethyl 3-[(ethoxycarbonyl)amino]-1-methyl-6-(phenylmethoxy)-1H-indole-2-carboxylate 7.5 g (0.088 mol) of sodium hydrogencarbonate and then 8.3 ml (0.076 mol) of ethyl chloroformate are added to a solution of 24 g (0.074 mol) of ethyl 3-amino-1-methyl-6-(phenylmethoxy)-1K-indole-2-carboxylate in 180 ml of a 9/1 mixture of tetrahydrofuran and water, while maintaining the temperature below 25° C. The mixture is left at room temperature for one hour and the solvent is then evaporated under reduced pressure. The residue is taken up in dichloromethane, washed with water and dried over sodium sulphate and the solvent is evaporated under reduced pressure. 28.2 g of product are recovered.

Melting point: 124–125° C.

17.6. 3-[(Ethoxycarbonyl)amino]-1-methyl-6-(phenylmethoxy)-1H-indole-2-carboxylic acid A suspension of 28.1 g (0.0708 mol) of ethyl 3-[(ethoxycarbonyl)amino]-1-methyl-6-(phenylmethoxy)-1H-indole-2-carboxylate in 170 ml of 96° ethanol is brought to reflux. 64 ml of a 10% ethanolic potassium hydroxide solution and 50 ml of tetrahydrofuran are added to this mixture. The suspension is left at reflux for 150 min, is then concentrated under reduced pressure, diluted with a mixture of water and ice and acidified with 6N hydrochloric acid. The product is then extracted with a mixture of dichloromethane and tetrahydrofuran, the organic phase is washed with water and dried over sodium sulphate and the solvent is evaporated under reduced pressure. The residue is triturated in diisopropyl ether and 24.8 g of product are recovered.

Melting point: 180° C. (decomposition).

17.7. Ethyl (1-methyl-6-(phenylmethoxy)-1H-indol-3-yl) carbamate 24.6 g (0.066 mol) of 3-[(ethoxycarbonyl)amino]-1-methyl-6-(phenylmethoxy)-1H-indole-2-carboxylic acid are heated at a temperature of the order of 180–185° C. for three minutes, the residue is then triturated in tetrahydrofuran and filtered and the filtrate is concentrated under reduced pressure. The product is purified by chromatography on silica gel, elution being carried out with an 80/20 mixture of cyclohexane and ethyl acetate. 18.3 g of product are recovered.

Melting point: 140–142° C.

17.8. (R)-5-(Methoxymethyl)-3-[1-methyl-6-(phenylmethoxy)-1H-indol-3-yl]oxazolidin-2-one A mixture comprising 9.1 g (0.028 mol) of ethyl [1-methyl-6-(phenylmethoxy)-1H-indol-3-yl)carbamate, 6.6 g (0.05 mol) of (S)-4-(methoxymethyl)-1,3-dioxolan-2-one and 1.16 g (0.0084 mol) of potassium carbonate in 180 ml of N,N-dimethylformamide is heated for 14 hours at 140° C. The solvent is evaporated under reduced pressure and the product is purified by chromatography on silica gel with a 50/50 mixture of cyclohexane and ethyl acetate. 6 g of product are recovered, which product exists in the form of a gum.

$[\alpha]_D^{20}$=−44.1° (c=1, methanol).

(S)-5-(Methoxymethyl)-3-[1-methyl-6-(phenylmethoxy)-1H-indol-3-yl]oxazolidin-2-one was prepared from (R)-4-(methoxymethyl)-1,3-dioxolan-2-one according to the same process, which product exists in the form of an oil.

$[\alpha]_D^{20}$=+41.5° (c=1, methanol).

EXAMPLE 18

(S,R)-5-(Methoxymethyl)-3-[1-methyl-6-(4,4.4-trifluoro-3-hydroxybutoxy)-1H-indol-3-yl] oxazolidin-2-one 18.1. (S)-5-(Methoxymethyl)-3-[1-methyl-6-hydroxy-1H-indol-3-yl]oxazolidin-2-one A solution of 1 g (0.0027 mol) of (S)-5-(methoxymethyl)-3-[1-methyl-6-(phenylmethoxy)-1H-indol-3-yl]oxazolidin-2-one, obtained in Example 17, in a mixture of 15 ml of N,N-dimethylformamide and 15 ml of ethanol is catalytically hydrogenated. The hydrogenation is carried out for 18 hours, under a normal hydrogen pressure, in the presence of 0.2 g of palladium-on-charcoal. The reaction mixture is filtered to remove the palladium-on-charcoal, the solvent is evaporated under reduced pressure and 0.53 g of product is recovered, which product exists in the form of a gum.

18.2. (S,R)-5-(Methoxymethyl)-3-[1-methyl-6-(4,4,4-trifluoro-3-hydroxybutoxy)-1H-indol-3-yl]oxazolidin-2-one A mixture of 0.30 g (0.00108 mol) of (S)-5-(methoxymethyl)-3-[1-methyl-6-hydroxy-1-H-indol-3-yl] oxazolidin-2-one, 0.34 g (0.00114 mol) of (R)-4,4,4-trifluoro-3-hydroxybutyl tosylate and 0.3 g (0.00217 mol) of potassium carbonate in 5 ml of acetonitrile is stirred at reflux for 90 min. The mixture is then diluted with dichloromethane and filtered and the filtrate is concentrated under reduced pressure. The organic phase is washed with water, dried over sodium sulphate and evaporated under reduced pressure. The residue is purified by chromatography on a silica column with a 95/5 mixture of dichloromethane and methanol. 0.27 g of product is recovered, which product exists in the form of gum.

Melting point: 80.5–82.0° C.

$[\alpha]_D^{20}$=+68.1° (c=1, methanol).

Compounds according to the invention and their physical characteristics are listed in the following table. These compounds were prepared according to the processes described above. In the solvent column, the solvent used to measure the optical rotation $[\alpha]^{20}$ has been shown (with c=1, except when otherwise indicated).

TABLE (I)

[Structure: 5-(OR₂-methyl)-oxazolidin-2-one with N-3 attached to benzofuran/indole (X) at position 3, with R₁Z at position 6]

| No. | R₁Z | R₂ | X | Config. | M.p. (° C.) | [α]_D^{20} | Solvent |
|---|---|---|---|---|---|---|---|
| 1 | C₆H₅—CH₂O | CH₃ | O | 5(R) | 112.6–112.8 | −34° | dichloromethane |
| 2 | | | | 5(S) | 111.9 | +33.3° | dichloromethane |
| 3 | HO | CH₃ | O | 5(R) | 136.0–136.5 | −55.3° | methanol |
| 4 | | | | 5(S) | 141.2 | +50.5° | methanol |
| 5 | HO | H | O | 5(R) | 172.1–172.2 | −39.3° | dimethyl sulphoxide |
| 6 | | | | 5(S) | 188.1–188.2 | +39.9 | dimethyl sulphoxide |
| 7 | CF₃—(CH₂)₃O | CH₃ | O | 5(R) | 92.6–93.0 | −30.3° | dichloromethane |
| 8 | | | | 5(S) | 93.6 | +28.6° | dichloromethane |
| 9 | CF₃—(CH₂)₃O | H | O | 5(R) | 194.0 | −26.7° | dimethyl sulphoxide |
| 10 | | | | 5(S) | 194.0–194.1 | +27.5° | dimethyl sulphoxide |
| 11 | CF₃—CH(OH)—(CH₂)₂O | CH₃ | O | 3(R), 5(R) | 80.5–82.0 | −5.3° | dichloromethane |
| 12 | | | | 3(R), 5(S) | 119.6–119.7 | +50.8° | dichloromethane |
| 13 | CF₃—CH(OH)—(CH₂)₂O | H | O | 3(R), 5(R) | 146–148 | −2.4° | dimethyl sulphoxide |
| 14 | | | | 3(R), 5(S) | 163.9–164.0 | +57.9° | dimethyl sulphoxide |
| 15 | CF₃—CH(OH)—(CH₂)₂O | CH₃ | O | 3(S), 5(R) | 119.7–119.8 | −51.1° | dichloromethane |
| 16 | | | | 3(S), 5(S) | 81.1–81.7 | +5.3° | dichloromethane |
| 17 | CF₃—CH(OH)—CH₂O | CH₃ | O | 5(R) | 99.2–99.4 | −28.6° | dichloromethane |
| 18 | CH₃—(CH₂)₃O | CH₃ | O | 5(R) | 72.3–72.4 | −35.0 | dichloromethane |
| 19 | CN—(CH₂)₃O | CH₃ | O | 5(R) | 90.8–90.9 | −33.7° | dichloromethane |
| 20 | cyclopropyl-CH₂O | CH₃ | O | 5(R) | 139.9–140.0 | −39.2° | dichloromethane |
| 21 | | | | 5(S) | 141.5 | +35.3° | dichloromethane |
| 22 | 1-hydroxycyclopentyl-CH₂O | CH₃ | O | 5(R) | 85.1–85.5 | −30.8° | dichloromethane |
| 23 | 4-F-C₆H₄—CH₂O | CH₃ | O | 5(R) | 92.7–92.8 | −31.0° | dichloromethane |
| 24 | C₆H₅—CH₂O | H | O | 5(S) | 171.4–171.6 | +29.1° | dimethyl sulphoxide |
| 25 | CH₃CH(OH)—(CH₂)₂O | CH₃ | O | 5(S) | 63.0–63.3 | +33.1° | dichloromethane |
| 26 | | | | 5(R) | 65.3–65.6 | −34.0° | dichloromethane |
| 27 | 3-Cl-C₆H₄—CH₂O | CH₃ | O | 5(S) | 67.2–67.8 | +28.8° | dichloromethane |

TABLE-continued (I)

$$\text{structure: 5-(OR}_2\text{-methyl)-3-(6-R}_1\text{Z-benzofuran/indole-3-yl)oxazolidin-2-one}$$

| No. | R₁Z | R₂ | X | Config. | M.p. (°C.) | $[\alpha]_D^{20}$ | Solvent |
|---|---|---|---|---|---|---|---|
| 28 | 3-(OCH₂-)benzyl-OCH₂- (CH₂O-Ph-OCH₂) | CH₃ | O | 5(S) | 100.6–101.0 | +31.0° | dichloromethane |
| 29 | 3-cyanobenzyl-OCH₂- | CH₃ | O | 5(S) | 126.6 | +30.2° | dichloromethane |
| 30 | 4-nitrobenzyl-OCH₂- | CH₃ | O | 5(S) | 161.3–161.6 | +28.4 | dichloromethane |
| 31 | 4-chlorobenzyl-OCH₂- | CH₃ | O | 5(S) | 104.6 | +29.7° | dichloromethane |
| 32 | 4-methoxybenzyl-OCH₂- | CH₃ | O | 5(S) | 107.9–108.5 | +30.6 | dichloromethane |
| 33 | 3-cyanobenzyl-OCH₂- | CH₃ | O | 5(R) | 126.4–126.5 | −29.8° | dichloromethane |
| 34 | 4-fluorobenzyl-OCH₂- | CH₃ | O | 5(S) | 94.0–94.1 | +31.1° | dichloromethane |

TABLE-continued (I)

[Structure: oxazolidinone ring with OR₂ group attached at 5-position via CH₂O, linked at N to an indole/benzofuran system (X) with R₁Z substituent at 6-position]

| No. | R₁Z | R₂ | X | Config. | M.p. (° C.) | $[\alpha]_D^{20}$ | Solvent |
|---|---|---|---|---|---|---|---|
| 35 | (tetrahydropyran-3-yl)CH₂O | CH₃ | O | 5(R) | 118.3–118.7 | −31.7° | dichloromethane |
| 36 |  | CH₃ | O | 5(S) | 117.2–117.4 | +31.2° | dichloromethane |
| 37 | H₃C=CH | CH₃ | O | 5(R) | 89.0–89.1 | −49.4° | dichloromethane |
| 38 | CF₃CH(OH)CH₂CH=CH | CH₃ | O | 3(R), 5(R) trans | 116.5–116.8 | −15.1° | dichloromethane |
| 39 | CF₃CH(OH)CH₂CH₂CH₂ | CH₃ | O | 3(R), 5(R) | 85.8–86.2 | −18.0° | dichloromethane |
| 40 | CF₃—CH₂CH₂—CH=CH | CH₃ | O | 5(R), cis/trans | 57–63 | −36.3° | dichloromethane |
| 41 | CF₃—CH₂CH₂CH₂CH₂ | CH₃ | O | 5(R) | 65.7–65.9 | −31.6° | dichloromethane |
| 42 | 2-phenylethenyl | CH₃ | O | 5(R), trans | 179.0–179.6 | −34.4° | dimethyl sulphoxide |
| 43 | 2-phenylethyl | CH₃ | O | (R) | 97.0–97.3 | −35.4° | dichloromethane |
| 44 | CF₃—(CH₂)₃O | H | S | 5(R) | 107.0–107.2 | −20.5° | dichloromethane |
| 45 | CF₃—(CH₂)₃O | CH₃ | S | 5(R) | oil | −21.8° | dichloromethane |
| 46 |  |  |  | 5(S) | oil | +21.1° | dichloromethane |
| 47 | C₆H₅—CH₂O | CH₃ | S | 5(R) | oil | −18.9° | dichloromethane |
| 48 |  |  |  | 5(S) | 73.8–74.2 | +23.9° | dichloromethane |
| 49 | CF₃—CH(OH)(CH₂)₂O | CH₃ | S | 3(R), 5(R) | oil | −1.8° | dichloromethane |
| 50 |  |  |  | 3(R), 5(S) | oil | +3.9° | dichloromethane |
| 51 | C₆H₅—CH₂O | CH₃ | NCH₃ | 5(R) | oil | −44.1° | methanol |
| 52 |  |  |  | 5(S) | oil | +41.5° | methanol |
| 53 | CF₃—(CH₂)₃O | CH₃ | NCH₃ | 5(R) | oil | −37.0° | methanol |
| 54 |  |  |  | 5(S) | oil | +36.7° | methanol |
| 55 | CF₃—CH(OH)—(CH₂)₂O | CH₃ | NCH₃ | 3(R), 5(R) | oil | −9.6° | methanol |
| 56 |  |  |  | 3(R), 5(S) | oil | +68.1° | methanol |

[a]: c = 0.5

In the table, the notation 3(R) or 3(S) relates to the configuration of the chiral carbon of the R₁Z group and the notation 5(R) or 5(S) relates to the configuration of the chiral carbon in the 5-position of the oxazolidinone ring.

The compounds of the invention have formed the subject of pharmacological tests which make it possible to determine their inhibiting power for monoamine oxidase A and for monoamine oxidase B.

The MAO-A and MAO-B activities were measured in vitro by using a rat brain homogenate as enzyme source, according to the method described by C. Fowler and M. Strolin-Benedetti in J. Neurochem., 40, 1534–1541 (1983).

The standard quantitative determination consists in homogenizing the rat brain in 20 volumes of 0.1M phosphate buffer (pH=7.4) and in preincubating 100 μl of homogenate (5 mg of tissue) at 37° C. for 20 minutes, in the absence or in the presence of different concentrations of the inhibitor studied. The reaction is initiated by the addition of [$^{14}$C]serotonin ([$^{14}$C]5HT, final concentration 125 μM), for the measurement of the MAO-A activity, or of [$^{14}$C] phenylethylamine ([$^{14}$C]PEA, final concentration 8 μM), for the measurement of the MAO-B activity, in a final volume of 500 μl. After incubating for 5 minutes in the case of [$^{14}$C]5HT and incubating for 1 minute in the case of [$^{14}$C] PEA, the reaction is halted by addition of 200 μl of 4N hydrochloric acid. The radioactive metabolites resulting from the oxidative deamination are then separated from the unconverted substrate, by extraction into an organic phase, and quantified by counting the radioactivity. The inhibitory activities with respect to MAO-A and MAO-B are given respectively by the inhibition constants Ki (MAO-A) and Ki (MAO-B). For the compounds of the invention, the Ki (MAO-A) values vary between 1.2 nM and values greater than 1000 nM whereas the Ki (MAO-B) values vary between 0.3 nM and values greater than 1000 nM. Some compounds of the invention are selective inhibitors of MAO-B, it being possible for the Ki (MAO-A)/Ki (MAO-B) ratio to be greater than 10³. Some compounds of the invention are selective inhibitors of MAO-A, it being possible for the Ki (MAO-B)/Ki (MAO-A) ratio to be greater than 10³. Others are mixed inhibitors of MAO-A and of MAO-B, it being possible for the Ki (MAO-A)/Ki (MAO-B) ratio to be between 0.1 and 10.

The results obtained show that the compounds of the invention can be used for the preparation of medicaments which are selective inhibitors of MAO-A or of MAO-B or which are mixed inhibitors of MAO-A and of MAO-B, these medicaments being employed in therapeutics, in particular in the treatment of depressive states of any nature, senile depressive psychoses, hypobulia, social phobias or mood disorders, in the improvement in general cerebral behaviour, in the prevention and the treatment of neurodegenerative diseases, such as Parkinson's disease and Alzheimer's disease, and all memory disorders, in anxiety, panic attacks, treatment of dependence and weaning related to the consumption of alcohol, of tobacco and/or of narcotics, and loss of appetite.

The compounds of the invention can be presented, in combination with excipients, in the form of compositions formulated for the purpose of oral, parenteral or rectal administration, for example in the form of tablets, dragées, capsules, solutions, suspensions or suppositories.

The dose of active principle administered is generally between 0.01 and 50 mg/kg/day, taken one or a number of times.

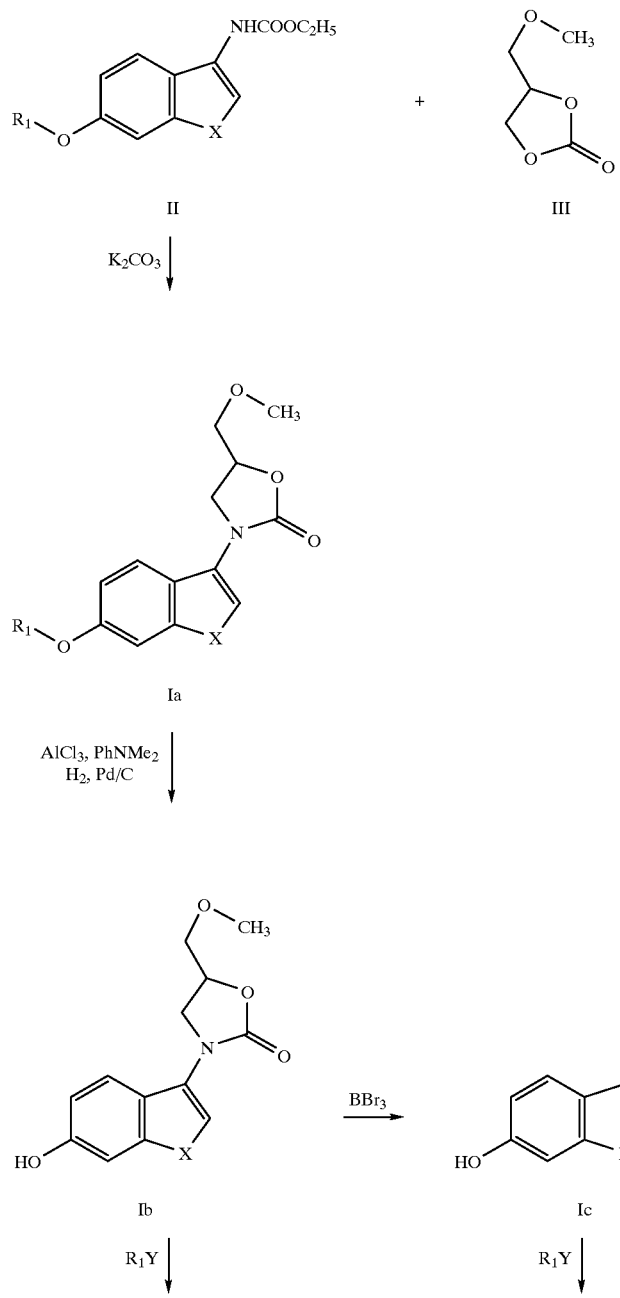

Appendix 1

-continued
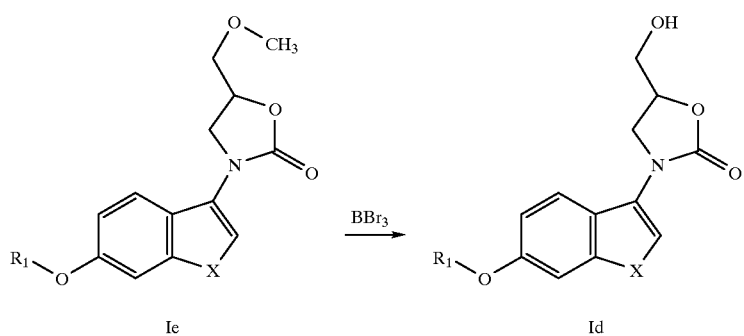
Appendix 2
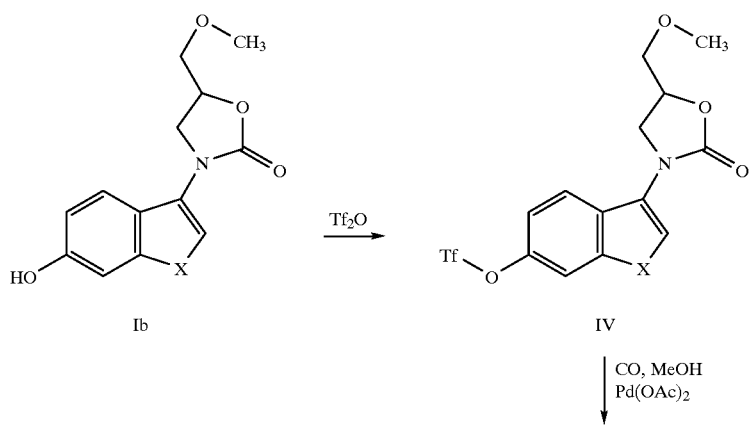
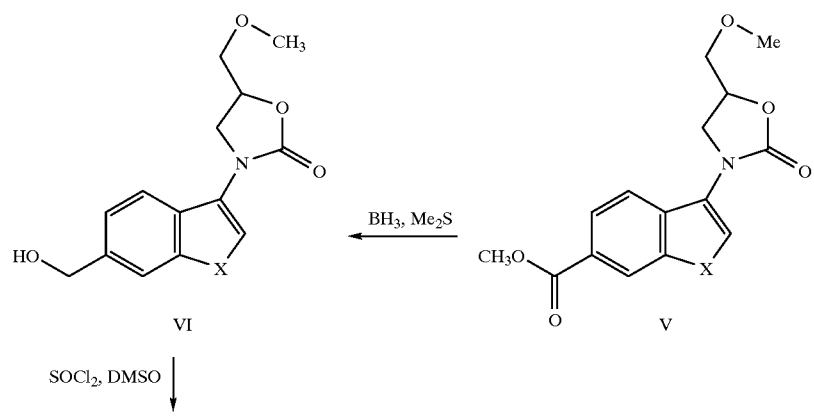

-continued
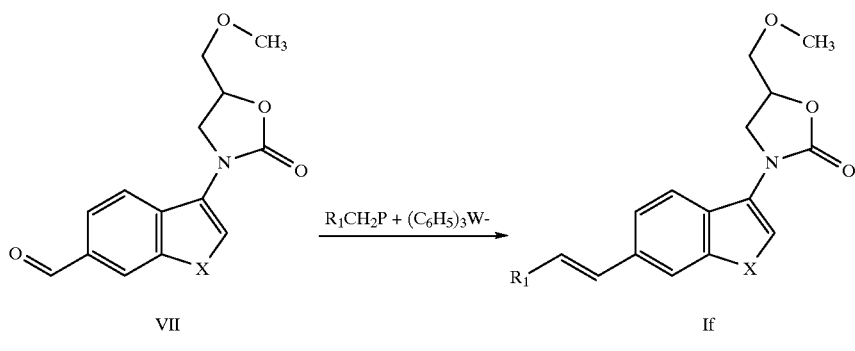
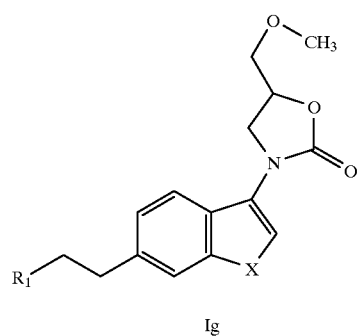
Appendix 3
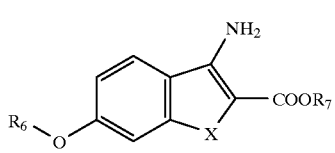
XII
ClCOOC$_2$H$_5$ ↓
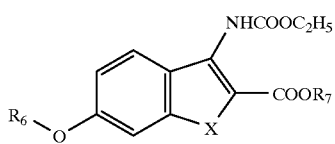
XI
KOH ↓
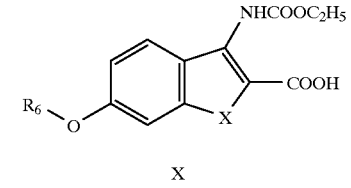
X
T° ↓
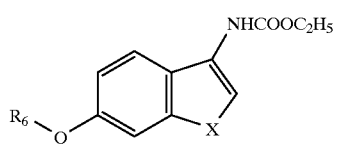
IX
BBr$_3$ ↓

-continued
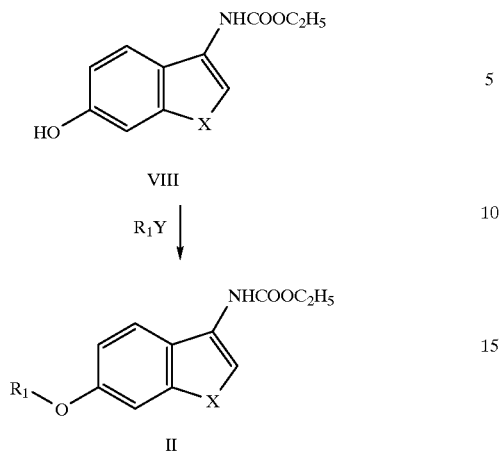
Appendix 4
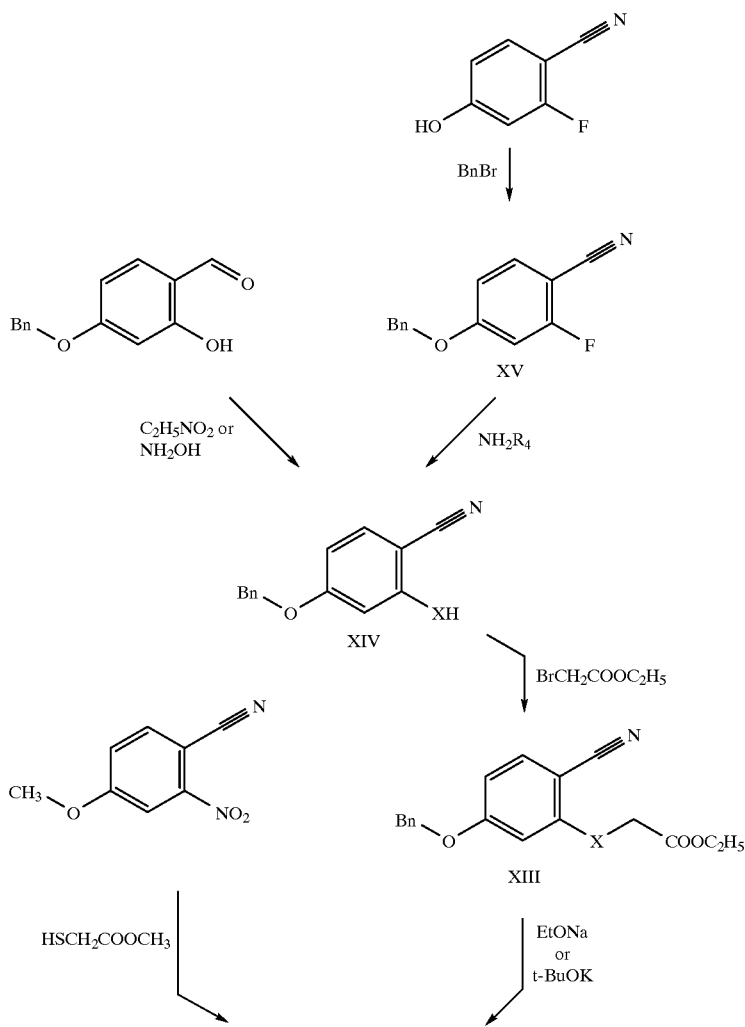

-continued

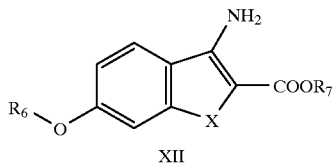

XII

We claim:
1. A compound of formula (I)

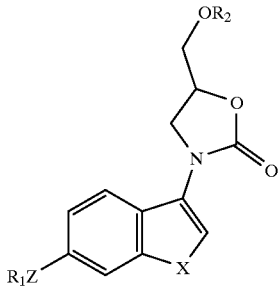

(I)

in which:
R$_1$ represents a hydrogen atom, an alkyl group, a hydroxyalkyl group, a fluoroalkyl group, a hydroxyfluoroalkyl group, a cyanoalkyl group, a phenyl group which is unsubstituted or substituted by a halogen atom or by an alkoxy, nitrile or nitro group, a phenylmethyl group which is unsubstituted or substituted by a halogen atom or by an alkoxy, nitrile or nitro group or an R$_3$A- group in which R$_3$ is a cycloalkyl or cyclooxyalkyl group which is unsubstituted or substituted by a hydroxyl group and A is a —CH$_2$ or —CH$_2$—CH$_2$ radical, R$_2$ represents a hydrogen atom or a methyl group, X represents an oxygen or sulphur atom or an NR$_4$ group where R$_4$ is an alkyl group or a hydrogen atom and Z represents an oxygen atom or a —CH=CH or —CH$_2$—CH$_2$ group, the said compounds existing in the form of pure enantiomers or diastereoisomers or of a mixture of these different forms.

2. A compound according to claim 1, wherein R$_2$ is a methyl group.

3. A compound according to claim 2, wherein X represents an oxygen atom.

4. A compound according to claim 1 wherein, when X represents an oxygen atom, the R$_1$Z group represents:
either, i) an R$_a$O group, where R$_a$ has one of the meanings of R$_1$ chosen from a hydrogen atom, an alkyl group, a fluoroalkyl group, a hydroxyfluoroalkyl group, a cyanoalkyl group, an R$_3$A- group, a phenyl group which is unsubstituted or substituted by a halogen atom or a nitro, nitrile or alkoxy group and a phenylmethyl group which is unsubstituted or substituted by a halogen atom or a nitro, nitrile or alkoxy group,
or, ii) an R$_b$Z group, where Z is a —CH=CH— or —CH$_2$—CH— group and R$_b$ has one of the meanings of R$_1$ chosen from a hydrogen atom or an alkyl group, a fluoroalkyl group, a hydroxyalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or a nitro, nitrile or alkoxy group.

5. A compound according to claim 4, wherein R$_a$ is a hydrogen atom or a phenylmethyl, butyl, 4,4,4-trifluorobutyl, 4,4,4-trifluoro-3-hydroxybutyl, 3,3,3-trifluoro-2-hydroxypropyl, 3-cyanopropyl, p-fluorophenylmethyl, cyclopropylmethyl or 2-(1-hydroxycyclopentyl)ethyl group.

6. A compound according to claim 4, wherein R$_b$Z is chosen from the ethenyl, 2-phenylethenyl, 2-phenylethyl, 5,5,5-trifluoropentyl, 5,5,5-trifluoropentenyl, 5,5,5-trifluoro-4-hydroxypentyl or 5,5,5-trifluoro-4-hydroxypentenyl group.

7. A compound according to claim 1 wherein, when X represents a sulphur atom, the R$_1$Z group represents an R$_c$O group, where R$_c$ has one of the meanings of R$_1$ chosen from an alkyl group, a hydroxyalkyl group, a fluoroalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or by an alkoxy, nitrile or nitro group.

8. A compound according to one of claim 1, wherein, when X represents an NR$_4$ group, R$_4$ is a methyl group and the R$_1$Z group represents an R$_d$O group, where R$_d$ has one of the meanings of R$_1$ chosen from a fluoroalkyl group, a hydroxyfluoroalkyl group, a phenyl group which is unsubstituted or substituted by a halogen atom or a nitro, nitrile or alkoxy group or a phenylmethyl group which is unsubstituted or substituted by a halogen atom or a nitro, nitrile or alkoxy group.

9. A compound according to claim 1, wherein, when Z represents a —CH=CH group and R$_1$ does not represent a hydrogen atom, the said compounds exist in the cis or trans form or in the form of a cis/trans mixture.

10. (R)-5-(Methoxymethyl)-3-[6-(phenylmethoxy)benzofuran-3-yl]oxazolidin-2-one or its enantiomer.

11. (R)-5-(Methoxymethyl)-3-[6-(4,4,4-trifluorobutoxy)benzofuran-3-yl]oxazolidin-2-one or its enantiomer.

12. (R,R)-5-Methoxymethyl)-3-[6-(4,4,4-trifluoro-3-hydroxybutoxy)benzofuran-3 -yl]oxazolidin-2-one or its diastereoisomers.

13. (R,R)-5-(Hydroxymethyl)-3-[6-(4,4,4-trifluoro-3-hydroxybutoxy)benzofuran-3-yl]oxazolidin-2-one or its diastereoisomers.

14. (R)-5-(Methoxymethyl)-3-[6-(5,5,5-trifluoropentyl)benzofuran-3-yl]oxazolidin-2-one or its enantiomer.

15. (R)-5-(Methoxymethyl)-3-[6-(5,5,5-trifluoro-4-hydroxypent-1-enyl)benzofuran-3-yl]-oxazolidin-2-one, its diastereoisomers or their cis or trans isomers.

16. (R)-5-(Methoxymethyl)-3-[6-(phenylmethoxy)benzo[b]thien-3-yl]oxazolidin-2-one or its enantiomer.

17. A compound according to claim 1, wherein the compound is (R)-5-(Methoxymethyl)-3-[6-(cyclopropylmethoxy)benzofuran-3-yl]oxazolidin-2-one or its enantiomer, (R)-5-(Methoxymethyl)-3-[6-(4,4,4-trifluorobutoxy)benzo[b]thien-3-yl]oxazolidin-2-one or its enantiomer, (R)-3-(6-Ethenylbenzofuran-3-yl)-5-(methoxymethyl)oxazolidin-2-one or its enantiomer, (R)-5-(Methoxymethyl)-3-[6-tetrahydropyranylmethoxy)benzofuran-3-yl]oxazolidin-2-one or its enantiomer, (R)-5-(Methoxymethyl)-3-[6-[4-cyano(propyloxy)]benzofuran-3-yl]oxazolidin-2-one or its enantiomer, (R)-5-(Methoxymethyl)-3-[6-[4-methoxy(phenylmethoxy)]benzofuran-3-yl]oxazolidin-2-one or its enantiomer, or (R)-5-(Methoxymethyl)-3-[6-[3-chloro(phenylmethoxy)]benzofuran-3-yl]oxazolidin-2-one or its enantiomer.

18. Process for the preparation of A compound according to claim 3 wherein an ethyl carbamate derivative of formula (II)

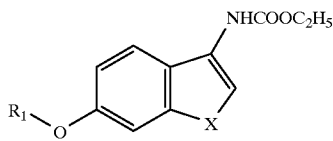

(II)

where $R_1$ represents an alkyl group, a hydroxyalkyl group, a fluoroalkyl group, a hydroxyfluoroalkyl group, a cyanoalkyl group, a phenyl group which is unsubstituted or substituted by a halogen atom or by an alkoxy, nitrile or nitro group, a phenylmethyl group which is unsubstituted or substituted by a halogen atom or by an alkoxy, nitrile or nitro group or an $R_3A$-group in which $R_3$ is a cycloalkyl or cyclooxyalkyl group which is unsubstituted or substituted by a hydroxyl group and A is —$CH_2$ or —$CH_2$—$CH_2$ radical, and X represents an oxygen or sulphur atom or an $NR_4$ group where $R_4$ is an alkyl group or a hydrogen atom, is reacted, in the presence of potassium carbonate, with 4-(methoxymethyl)-1,3-dioxolan-2-one of formula (III).

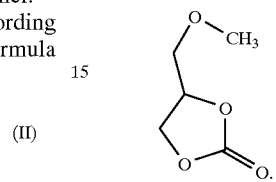

(III)

19. Medicament comprising a compound according to claim 1.

20. Pharmaceutical composition, comprising a compound according to claim 1, in combination with at least one pharmaceutically acceptable excipient.

* * * * *